US012397020B2

(12) United States Patent
You et al.

(10) Patent No.: US 12,397,020 B2
(45) Date of Patent: Aug. 26, 2025

(54) METHOD FOR DIRECT REPROGRAMMING OF URINE CELLS INTO NEURAL STEM CELLS USING SYNTHETIC MRNA

(71) Applicant: StemLab Inc., Seoul (KR)

(72) Inventors: Seung Kwon You, Yongin-si (KR); Phil Jun Kang, Seoul (KR); Da Ryeon Son, Gimhae-si (KR); Won Jun Hong, Seoul (KR); Won Jin Yun, Yongin-si (KR); Jang Bo Lee, Seoul (KR); Gyu Man Park, Seongnam-si (KR); In Yong Kim, Seoul (KR); Jung Hyun Park, Seoul (KR); Jie Zheng, Seoul (KR); Wei Wei Gao, Seoul (KR); Ji Hoon Jang, Jeonju-si (KR); Eun Kyoung Jun, Cheonan-si (KR); Byung Sun Yoon, Seoul (KR)

(73) Assignee: STEMLAB, INC., Seoul (KR)

( * ) Notice: Subject to any disclaimer, the term of this patent is extended or adjusted under 35 U.S.C. 154(b) by 675 days.

(21) Appl. No.: 17/271,873

(22) PCT Filed: Aug. 28, 2019

(86) PCT No.: PCT/KR2019/011014
§ 371 (c)(1),
(2) Date: Feb. 26, 2021

(87) PCT Pub. No.: WO2020/045990
PCT Pub. Date: Mar. 5, 2020

(65) Prior Publication Data
US 2021/0260132 A1    Aug. 26, 2021

(51) Int. Cl.
*A61K 35/30*    (2015.01)
*C12N 5/0797*    (2010.01)
*C12N 15/87*    (2006.01)

(52) U.S. Cl.
CPC ............ *A61K 35/30* (2013.01); *C12N 5/0623* (2013.01); *C12N 15/87* (2013.01); *C12N 2500/02* (2013.01); *C12N 2501/602* (2013.01); *C12N 2501/603* (2013.01); *C12N 2501/604* (2013.01); *C12N 2501/999* (2013.01); *C12N 2506/25* (2013.01)

(58) Field of Classification Search
CPC ...... A61K 35/30; C12N 5/0623; C12N 15/87; C12N 2500/02; C12N 2501/602; C12N 2501/603; C12N 2501/604; C12N 2501/999; C12N 2506/25
See application file for complete search history.

(56) References Cited

U.S. PATENT DOCUMENTS

| 10,011,819 B2 * | 7/2018 | Pan ........................ A61P 25/28 |
| 2015/0232810 A1 | 8/2015 | Luo et al. |
| 2017/0037376 A1 | 2/2017 | Pei et al. |

FOREIGN PATENT DOCUMENTS

| JP | 2015-509719 A | 4/2015 |
| KR | 20140138221 A | 12/2014 |
| WO | 2014145975 A2 | 9/2014 |

OTHER PUBLICATIONS

Maekawa, M., et al., "Direct reprogramming of somatic cells is promoted by maternal transcription factor Glis1," Nature 474(7350): 225-229. doi: 10.1038/nature10106. Jun. 8, 2011. (Year: 2011).*
Warren, L., et al., "Highly efficient reprogramming to pluripotency and directed differentiation of human cells with synthetic modified mRNA," Cell Stem Cell 7(5): 618-630. doi: 10.1016/j.stem.2010.08.012. (Year: 2010).*
Van Oosten, A. L., et al., "JAK/STAT3 signalling is sufficient and dominant over antagonistic cues for the establishment of naive pluripotency," Nat Commun 3: 817. doi: 10.1038/ncomms1822. (Year: 2012).*
Yamazaki K., et al., "Functional Comparison of Neuronal Cells Differentiated from Human Induced Pluripotent Stem Cell-Derived Neural Stem Cells under Different Oxygen and Medium Conditions," Journal of Biomolecular Screening 21(10):1054-1064. doi: 10.1177/1087057116661291. (Year: 2016).*
Felling, R. J., et al., "Astrocyte-produced leukemia inhibitory factor expands the neural stem/progenitor pool following perinatal hypoxia-ischemia," J Neurosci Res 94(12): 1531-1545. doi: 10.1002/jnr.23929. (Year: 2016).*
Maekawa, M., et al., "Direct reprogramming of somatic cells is promoted by maternal transcription factor Glis1," Nature 474(7350): 225-229. doi: 10.1038/nature10106. (Year: 2011).*
Nazir, F. H., et al., "Expression and secretion of synaptic proteins during stem cell differentiation to cortical neurons," Neurochem Int 121: 38-49. doi: 10.1016/j.neuint.2018.10.014. (Year: 2018).*
Simon, H. H., et al., "Midbrain dopaminergic neurons: control of their cell fate by the engrailed transcription factors," Cell Tissue Res 318(1): 53-61. doi: 10.1007/s00441-004-0973-8. (Year: 2014).*
Int'l Search Report and Written Opinion issued Nov. 29, 2019 in Int'l Application No. PCT/KR2019/011014, English translation of Int'l Search Report only.
Wang et al, "Using low-risk factors to generate nonintegrated human induced pluripotent stem cells from urine-derived cells," Stem Cell Research & Therapy, vol. 8, No. 245, pp. 1-13 (2017).
Cheng et al., "Generation of neural progenitor cells by chemical cocktails and hypoxia," Cell Research, vol. 24, pp. 665-679 (2014).
Extended European Search Report issued May 17, 2022 in EP Application No. 19856400.7.
Huang et al., "Human neural stem cells rapidly ameliorate symptomatic inflammation in early-stage ischemic-reperfusion cerebral injury," Stem Cell Research & Therapy, vol. 5, No. 129, pp. 1-16 (2014).

(Continued)

*Primary Examiner* — Tracy Vivlemore
*Assistant Examiner* — Eric J Rogers
(74) *Attorney, Agent, or Firm* — Panitch Schwarze Belisario & Nadel LLP

(57) ABSTRACT

A method for inducing reprogramming of neural stem cells from urine cells by introducing mRNAs of reprogramming factors Oct4, Sox2, Klf4, and Glis1 is disclosed. A composition for the prevention or treatment of neurological damage diseases with the neural stem cells induced by the method as an active ingredient is disclosed.

4 Claims, 15 Drawing Sheets

Specification includes a Sequence Listing.

(56) References Cited

OTHER PUBLICATIONS

Wang et al., "Generation of integration-free neural progenitor cells from cells in human urine," Nature Methods, vol. 10. No. 1, pp. 84-89 plus 2 pages (Jan. 2013).

Yoshioka et al., "Efficient Generation of Human iPCSs by a Synthetic Self-Replicative RNA," Cell Stem Cell, vol. 13, pp. 246-256 (Aug. 1, 2013).

Wang, et al., Using low-risk factors to generate non-integrated human induced pluripotent stem cells from urine-derived cells, Stem Cell Research & Therapy (2017) 8:245 DOI 10.1186/s 13287-017-0698-8.

Chinese Office Action dated Mar. 12, 2024 in Chinese Patent Application No. CN 2019800715359.

Li, et al., Rapid induction and long term self-renewal of primitive neural precursors from human embryonic stem cells by small molecule inhibitors, Proceedings of the National Academy of Sciences 2011, vol. 108, No. 20, pp. 8299-8304.

\* cited by examiner

Fig. 6
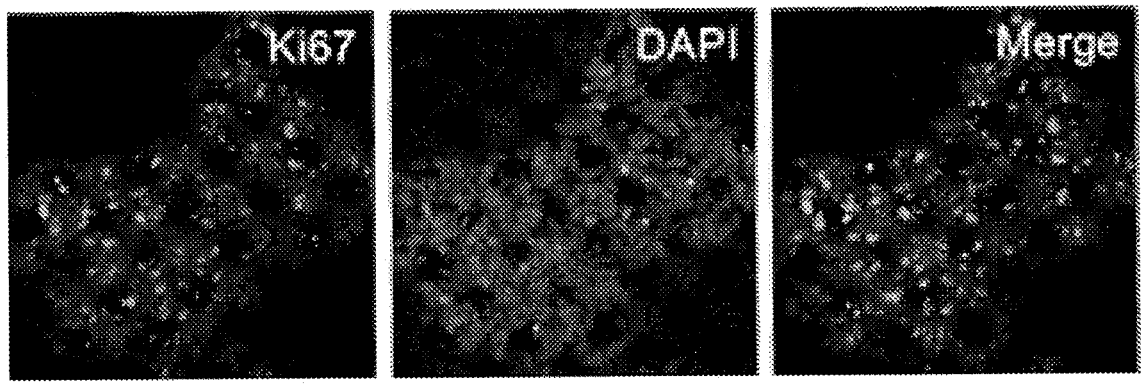
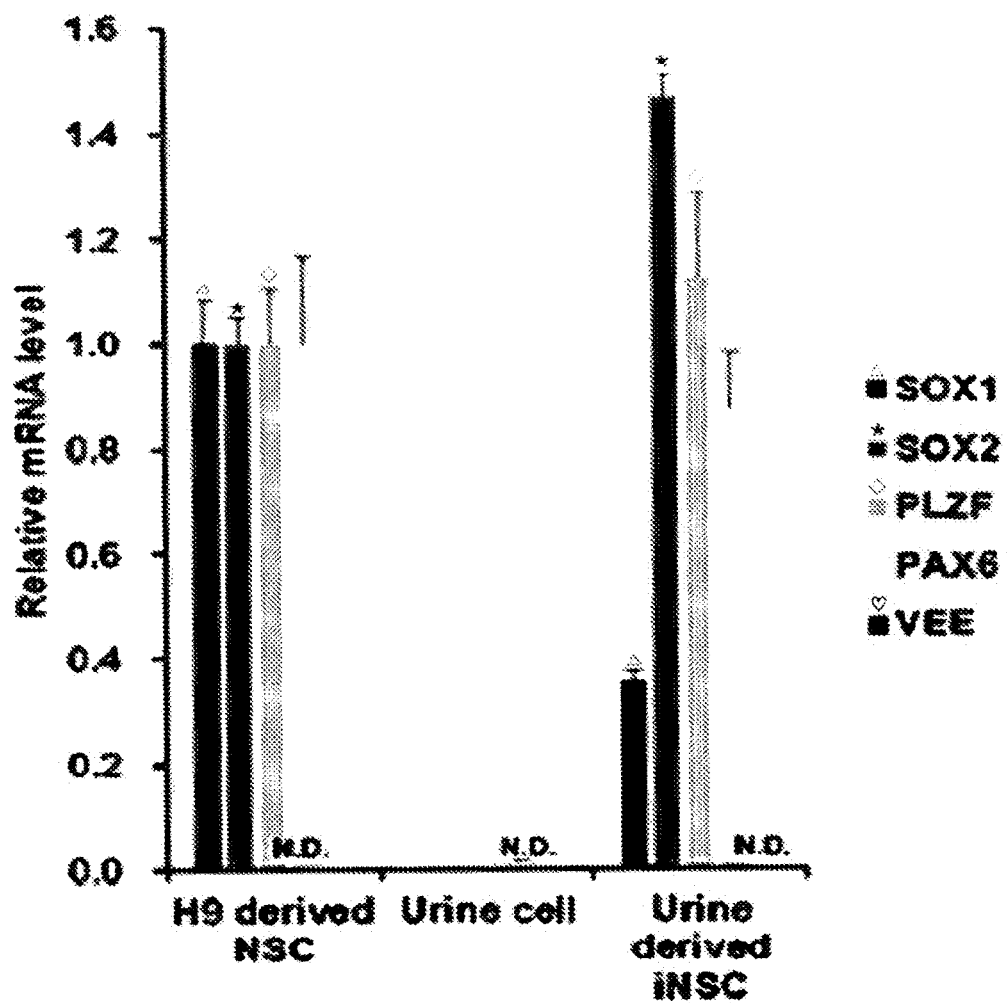
Fig. 7

Fig. 10d
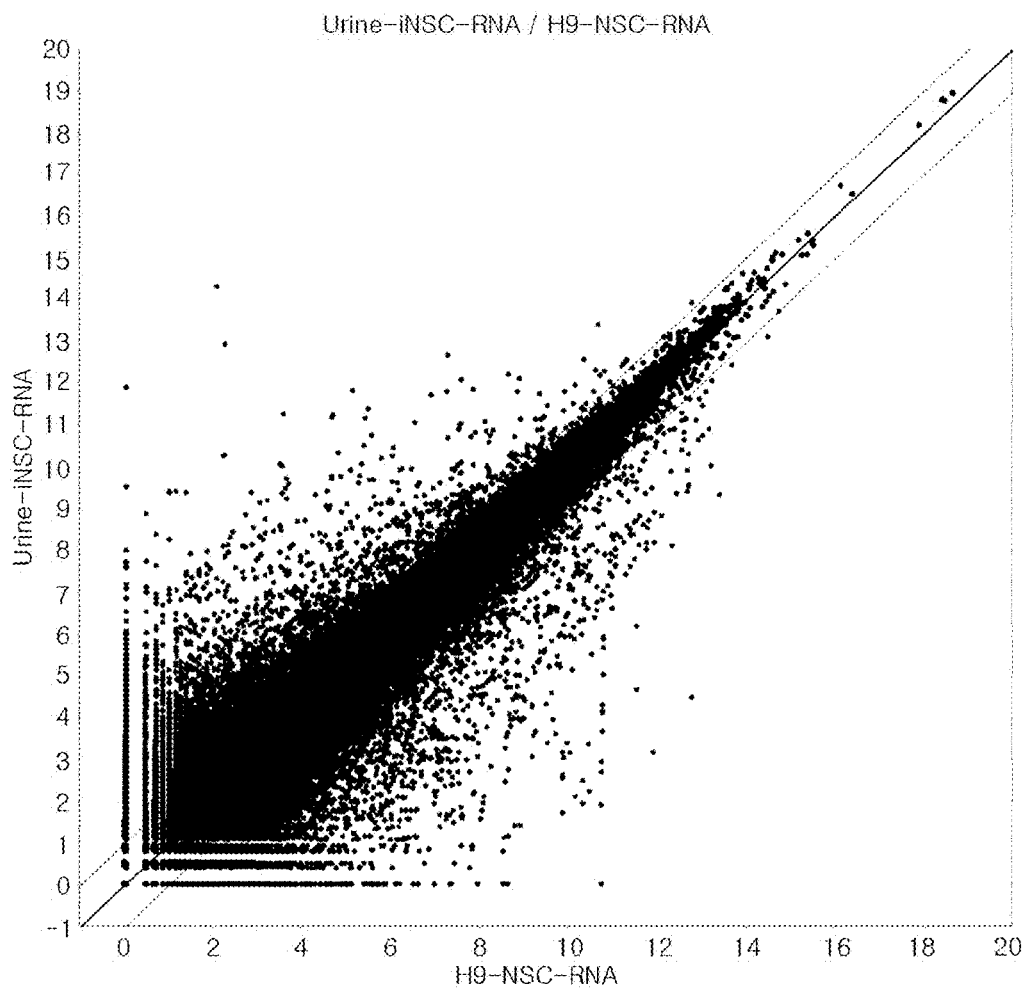
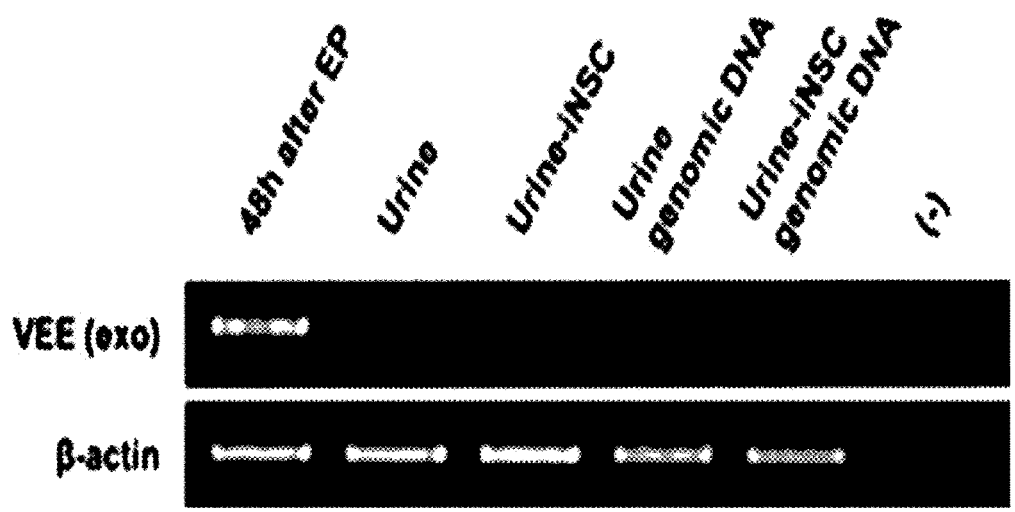
Fig. 11

Sample No.  1  2
Match Analysis

| Locus | Reference Database Profile | | Sample Profile | | Shared alleles # |
|---|---|---|---|---|---|
| | Database : Urine | | Sample Name : NSC | | |
| D5S818 | 8 | 9 | 8 | 9 | 2 |
| D13S317 | 9 | 13 | 9 | 13 | 2 |
| D7S820 | 11 | 12 | 11 | 12 | 2 |
| D16S539 | 11 | | 11 | | 1 |
| vWA | 16 | 17 | 16 | 17 | 2 |
| TH01 | 7 | 9 | 7 | 9 | 2 |
| TPOX | 9 | 11 | 9 | 11 | 2 |
| CSF1PO | 10 | 12 | 10 | 12 | 2 |
| AMEL | X | Y | X | Y | 2 |
| D3S1358 | 16 | | 16 | | 1 |
| D21S11 | 29 | 30 | 29 | 30 | 2 |
| D18S51 | 15 | 18 | 15 | 18 | 2 |
| D8S1179 | 12 | 13 | 12 | 13 | 2 |
| FGA | 21 | 21.2 | 21 | 21.2 | 2 |
| D2S1338 | 24 | 25 | 24 | 25 | 2 |
| D19S433 | 14.2 | 15 | 14.2 | 15 | 2 |
| Penta D | 9 | 12 | 9 | 12 | 2 |
| Penta E | 16 | 17 | 16 | 17 | 2 |
| *Number of shared alleles* | | | | | 34 |
| *Total number of alleles in the reference database profile* | | | | | 34 |
| *% match* | | | | | 100.0% |
| Result interpretation | | | | | Related |

Fig. 12

SEQUENCE LISTING

```
<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: SOX1 forward

<400> SEQUENCE: 1
acacttgaag cccagatgg                                                19
```

```
<210> SEQ ID NO 2
<211> LENGTH: 20
<212> TYPE: DNA
<213> ORGANISM: Artificial Sequence
<220> FEATURE:
<223> OTHER INFORMATION: SOX1 reverse

<400> SEQUENCE: 2
ataggctcac ttttggacgg                                                   20

<210> SEQ ID NO 3
<211> LENGTH: 22
<212> TYPE: DNA
<213> ORGANISM: Artificial Sequence
<220> FEATURE:
<223> OTHER INFORMATION: SOX2 forward

<400> SEQUENCE: 3
tcaggagttg tcaaggcaga ga                                                22

<210> SEQ ID NO 4
<211> LENGTH: 22
<212> TYPE: DNA
<213> ORGANISM: Artificial Sequence
<220> FEATURE:
<223> OTHER INFORMATION: SOX2 reverse

<400> SEQUENCE: 4
ccgccgccga tgattgttat ta                                                22

<210> SEQ ID NO 5
<211> LENGTH: 19
<212> TYPE: DNA
<213> ORGANISM: Artificial Sequence
<220> FEATURE:
<223> OTHER INFORMATION: PAX6 forward

<400> SEQUENCE: 5
ggctcaaatg cgacttcag                                                    19

<210> SEQ ID NO 6
<211> LENGTH: 23
<212> TYPE: DNA
<213> ORGANISM: Artificial Sequence
<220> FEATURE:
<223> OTHER INFORMATION: PAX6 reverse

<400> SEQUENCE: 6
cccttcgatt agaaaaccat acc                                               23

<210> SEQ ID NO 7
<211> LENGTH: 22
<212> TYPE: DNA
<213> ORGANISM: Artificial Sequence
<220> FEATURE:
<223> OTHER INFORMATION: PLZF forward

<400> SEQUENCE: 7
tatacagcca cgctgcaagc ca                                                22

<210> SEQ ID NO 8
<211> LENGTH: 22
<212> TYPE: DNA
<213> ORGANISM: Artificial Sequence
<220> FEATURE:
<223> OTHER INFORMATION: PLZF reverse
```

```
<400> SEQUENCE: 8
tggtctccag catcttcagg ca                                             22

<210> SEQ ID NO 9
<211> LENGTH: 22
<212> TYPE: DNA
<213> ORGANISM: Artificial Sequence
<220> FEATURE:
<223> OTHER INFORMATION: EMX1 forward

<400> SEQUENCE: 9
caggcccagg tagttcaatg gg                                             22

<210> SEQ ID NO 10
<211> LENGTH: 22
<212> TYPE: DNA
<213> ORGANISM: Artificial Sequence
<220> FEATURE:
<223> OTHER INFORMATION: EMX1 reverse

<400> SEQUENCE: 10
gctcagcctt aagccctgtc tc                                             22

<210> SEQ ID NO 11
<211> LENGTH: 22
<212> TYPE: DNA
<213> ORGANISM: Artificial Sequence
<220> FEATURE:
<223> OTHER INFORMATION: FOXG1 forward

<400> SEQUENCE: 11
acccgtcaat gacttcgcag ag                                             22

<210> SEQ ID NO 12
<211> LENGTH: 22
<212> TYPE: DNA
<213> ORGANISM: Artificial Sequence
<220> FEATURE:
<223> OTHER INFORMATION: FOXG1 reverse

<400> SEQUENCE: 12
agggttggaa gaagacccct ga                                             22

<210> SEQ ID NO 13
<211> LENGTH: 22
<212> TYPE: DNA
<213> ORGANISM: Artificial Sequence
<220> FEATURE:
<223> OTHER INFORMATION: OTX1 forward

<400> SEQUENCE: 13
ctcaaacaac ccccatacgg ca                                             22

<210> SEQ ID NO 14
<211> LENGTH: 22
<212> TYPE: DNA
<213> ORGANISM: Artificial Sequence
<220> FEATURE:
<223> OTHER INFORMATION: OTX1 reverse

<400> SEQUENCE: 14
ggtagcgagt cttggcgaag ag                                             22

<210> SEQ ID NO 15
```

```
<211> LENGTH: 24
<212> TYPE: DNA
<213> ORGANISM: Artificial Sequence
<220> FEATURE:
<223> OTHER INFORMATION: OTX2 forward

<400> SEQUENCE: 15
ttcagggctg tgtgaattgt gtga                                              24

<210> SEQ ID NO 16
<211> LENGTH: 24
<212> TYPE: DNA
<213> ORGANISM: Artificial Sequence
<220> FEATURE:
<223> OTHER INFORMATION: OTX2 reverse

<400> SEQUENCE: 16
cagaggtgga gttcaaggtt gcat                                              24

<210> SEQ ID NO 17
<211> LENGTH: 22
<212> TYPE: DNA
<213> ORGANISM: Artificial Sequence
<220> FEATURE:
<223> OTHER INFORMATION: EN1 forward

<400> SEQUENCE: 17
gagttccagg caaaccgcta ca                                                22

<210> SEQ ID NO 18
<211> LENGTH: 22
<212> TYPE: DNA
<213> ORGANISM: Artificial Sequence
<220> FEATURE:
<223> OTHER INFORMATION: EN1 reverse

<400> SEQUENCE: 18
gttgtacagt ccctgggcca tg                                                22

<210> SEQ ID NO 19
<211> LENGTH: 22
<212> TYPE: DNA
<213> ORGANISM: Artificial Sequence
<220> FEATURE:
<223> OTHER INFORMATION: GBX2 forward

<400> SEQUENCE: 19
cggttagcag ccacctttcc at                                                22

<210> SEQ ID NO 20
<211> LENGTH: 22
<212> TYPE: DNA
<213> ORGANISM: Artificial Sequence
<220> FEATURE:
<223> OTHER INFORMATION: GBX2 reverse

<400> SEQUENCE: 20
gacgtgcttc acatggctca ga                                                22

<210> SEQ ID NO 21
<211> LENGTH: 20
<212> TYPE: DNA
<213> ORGANISM: Artificial Sequence
<220> FEATURE:
<223> OTHER INFORMATION: HOXB2 forward
```

```
<400> SEQUENCE: 21
gagacccagg agccaaaagc                                                 20

<210> SEQ ID NO 22
<211> LENGTH: 20
<212> TYPE: DNA
<213> ORGANISM: Artificial Sequence
<220> FEATURE:
<223> OTHER INFORMATION: HOXB2 reverse

<400> SEQUENCE: 22
gaaggagacg tggcggattg                                                 20

<210> SEQ ID NO 23
<211> LENGTH: 22
<212> TYPE: DNA
<213> ORGANISM: Artificial Sequence
<220> FEATURE:
<223> OTHER INFORMATION: HOXB4 forward

<400> SEQUENCE: 23
ctgagggcca gaatgactgc tc                                              22

<210> SEQ ID NO 24
<211> LENGTH: 22
<212> TYPE: DNA
<213> ORGANISM: Artificial Sequence
<220> FEATURE:
<223> OTHER INFORMATION: HOXB4 reverse

<400> SEQUENCE: 24
cagaactcaa ctggcccctc ac                                              22

<210> SEQ ID NO 25
<211> LENGTH: 20
<212> TYPE: DNA
<213> ORGANISM: Artificial Sequence
<220> FEATURE:
<223> OTHER INFORMATION: VEE forward

<400> SEQUENCE: 25
acgaagggca agtcgctgtt                                                 20

<210> SEQ ID NO 26
<211> LENGTH: 20
<212> TYPE: DNA
<213> ORGANISM: Artificial Sequence
<220> FEATURE:
<223> OTHER INFORMATION: VEE reverse

<400> SEQUENCE: 26
tttcgtcggc ccagttggta                                                 20

<210> SEQ ID NO 27
<211> LENGTH: 24
<212> TYPE: DNA
<213> ORGANISM: Artificial Sequence
<220> FEATURE:
<223> OTHER INFORMATION: OCT4 forward

<400> SEQUENCE: 27
gacaggggga ggggaggagc tagg                                            24

<210> SEQ ID NO 28
```

```
<211> LENGTH: 26
<212> TYPE: DNA
<213> ORGANISM: Artificial Sequence
<220> FEATURE:
<223> OTHER INFORMATION: OCT4 reverse

<400> SEQUENCE: 28
cttccctcca accagttgcc ccaaac                                          26

<210> SEQ ID NO 29
<211> LENGTH: 20
<212> TYPE: DNA
<213> ORGANISM: Artificial Sequence
<220> FEATURE:
<223> OTHER INFORMATION: REX1 forward

<400> SEQUENCE: 29
ctgaagaaac gggcaaagac                                                 20

<210> SEQ ID NO 30
<211> LENGTH: 20
<212> TYPE: DNA
<213> ORGANISM: Artificial Sequence
<220> FEATURE:
<223> OTHER INFORMATION: REX1 reverse

<400> SEQUENCE: 30
gaacattcaa gggagcttgc                                                 20

<210> SEQ ID NO 31
<211> LENGTH: 25
<212> TYPE: DNA
<213> ORGANISM: Artificial Sequence
<220> FEATURE:
<223> OTHER INFORMATION: NANOG forward

<400> SEQUENCE: 31
cagccctgat tcttccacca gtccc                                           25

<210> SEQ ID NO 32
<211> LENGTH: 24
<212> TYPE: DNA
<213> ORGANISM: Artificial Sequence
<220> FEATURE:
<223> OTHER INFORMATION: NANOG reverse

<400> SEQUENCE: 32
ggaaggttcc cagtcgggtt cacc                                            24
```

METHOD FOR DIRECT REPROGRAMMING OF URINE CELLS INTO NEURAL STEM CELLS USING SYNTHETIC MRNA

CROSS-REFERENCE TO RELATED APPLICATIONS

This application is a Section 371 of International Application No. PCT/KR2019/011014, filed Aug. 28, 2019, which was published in the Korean language on Mar. 5, 2020 under International Publication No. WO 2020/045990 A1, which claims priority under 35 U.S.C. § 119 (b) to Korean Application No. 10-2018-0101208, filed Aug. 28, 2018, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "688588_39US_Sequence_Listing", creation date of Feb. 25, 2021, and having a size of 8 KB. The sequence listing submitted via EFS-Web is part of the specification and is herein incorporated by reference in its entirety.

TECHNICAL FIELD

The present invention relates to a method for direct reprogramming of urine cells into neural stem cells and a pharmaceutical composition for treating neurological damage diseases, comprising reprogrammed neural stem cells prepared by the method.

BACKGROUND ART

Stem cells refer to cells having unlimited potential towards self-renewal or differentiation related to specific cells and tissues required in the body. Stem cells are classified into three types: embryonic stem cells (ES cells) isolated from early embryos, embryonic germ cells (EG cells) isolated from embryonic primordial germ cells, and multipotent adult progenitor cells (MAPC cells) isolated from adult tissues.

Since stem cells have the potential to be differentiated into cells with specialized functions, they have been the subject of research for restoring the functions of various organs as cell therapeutic agents, and recently, their application has been expanding to the fields of plastic surgery and aesthetics.

The role of adult stem cells in vivo may be roughly summarized in two ways. First, stem cells themselves are differentiated into tissues and cells in our bodies and regenerate damaged tissues and cells, and second, stem cells continuously secrete growth factors and proteins such as cytokines during its lifespan to aid the growth and regeneration of neighboring cells.

Direct reprogramming is a technique which allows conversion of somatic cells into other types of cells as desired. Since direct reprogramming does not go through a pluripotent stem cell state unlike reprogramming according to Japanese Professor Yamanaka, it can save time and exhibit a high level of efficiency, while solving the risk related to tumorigenesis and the incurrence of cost of further differentiation of pluripotent stem cells. However, a direct reprogramming method currently performed mainly uses mouse cells as a cell source, so that the probability of being reproduced in the same manner in human somatic cells is not high. Further, skin cells (fibroblasts) are often used among human somatic cells, but in this case, an invasive method of collecting cell sources is required, and poses a risk of pain and safety to the donor, and convenience deteriorates. In addition, clinical use is difficult because viruses are mainly used by a method for introducing reprogramming factors (genes) required during direct reprogramming, and a gene integration system using viruses is not suitable for treatment, because the system induces mutations due to indiscriminate insertion into genomes.

Thus, the present inventors solved the aforementioned problems using human urine-derived cells which are easily collected as a cell source and using the transfection of synthetic mRNA for the cell introduction of reprogramming factors, and confirmed optimum culture conditions required for highly efficient direct reprogramming of neural stem cells from urine cells, thereby completing the present invention.

RELATED ART DOCUMENTS

Korean Patent Application Laid-Open No. 10-2013-0087020

DISCLOSURE

Technical Problem

An object of the present invention is to provide a composition for direct reprogramming of urine cells into neural stem cells.

Another object of the present invention is to provide a method for direct reprogramming of urine cells into neural stem cells.

Still another object of the present invention is to provide a method for the prevention or treatment of neurological damage diseases comprising administering neural stem cells reprogrammed from urine cells as an active ingredient.

Still another object of the present invention is to provide a pharmaceutical composition for the prevention or treatment of neurological damage diseases comprising neural stem cells reprogrammed from urine cells as an active ingredient.

Technical Solution

The present invention provides a composition a composition for direct reprogramming of urine cells into neural stem cells, the composition comprising:
(i) an Oct4 protein or a nucleic acid encoding the Oct4 protein;
(ii) a Sox2 protein or a nucleic acid encoding the Sox2 protein;
(iii) a Klf4 protein or a nucleic acid encoding the Klf4 protein; and
(iv) a Glis1 protein or a nucleic acid encoding the Glis1 protein.

As used herein, the term "reprogrammed neural stem cells" includes neural stem cells made by direct reprogramming for establishing an undifferentiated stem cell having a multi-potent ability similar to or the same as that of neural stem cells. Induced neural stem cells have the same or similar characteristics as neural stem cells, specifically may show a similar cell morphology, have a similar gene and protein expression pattern, and have a multi-potent ability in vivo and in vitro. Therefore, the reprogrammed neural stem cells of the present invention may be those which can be differentiated into nerve cells (neurons), astrocytes, oligodendrocytes, GABAergic nerve cells, dopaminergic nerve cells, or the like.

As used herein, the term "urine cells (UCs)" is known as somatic cells that can be readily and repeatedly obtained at any time without any inconvenience and pain.

The present inventor found that when reprogramming factors Oct4, Sox2, Klf4, and Glis1 are expressed in urine cells, urine cells that are already differentiated cell types are reprogrammed into neural stem cells having differentiation capacity.

The term "reprogramming factors" started from reprogramming which is a concept introduced by Yamanaka in 2006. All cells of an adult are gradually differentiated in an undifferentiated state while going through a normal development process, and thus changed into cells whose respective functions are specialized. Among them, fertilized cells are totipotent, and can be divided into an inner cell mass and outer cells when the fertilized cells become blastocysts as the subsequent development step proceeds, and in this case, inner cell mass cells can give rise to embryonic cells and germ cells, which are called pluripotent. The embryonic stem cells exhibit a pluripotent-specific gene expression aspect, and representative examples thereof include Oct4, Sox2, Nanog, Lin28, and the like. Reprogramming can be said to be a technique that induces such specific gene expression in somatic cells to restore properties similar to those of undifferentiated cells such as embryonic stem cells and adult stem cells. Oct4, Sox2, Klf4 and Glis1 were used by the inventor to reprogram urine cells into neural stem cells as a part of various factors that have been used in a series of studies related to reprogramming.

Oct4, Sox2, Klf4, and Glis1 used in the compositions of the present invention include all Oct4, Sox2, Klf4 and Glis1 derived from humans and animals such as horses, sheep, pigs, goats, camels, antelopes, and dogs, and are preferably human Oct4, Sox2, Klf4, and Glis1. Further, the Oct4, Sox2, Klf4, and Glis1 proteins of the present invention used for reprogramming into neural stem cells may include proteins having wild type amino acid sequences thereof, but also variants of Oct4, Sox2, Klf4, and Glis1 proteins.

In a specific exemplary embodiment, the gene sequences of Oct4, Sox2, Klf4 and Glis1 first used in reprogramming and disclosed in Nature. 2011 Jun. 8; 474 (7350): 225-9 were used.

The variants of Oct4, Sox2, Klf4, and Glis1 proteins refer to proteins in which at least one amino acid residue differs from the native amino acid sequences of Oct4, Sox2, Klf4, and Glis1 by deletion, insertion, non-conservative or conservative substitution, or a combination thereof. The variant may be a functional equivalent that shows the same biological activity as a native protein, or may be a variant in which physical and chemical properties of a protein are modified as necessary. The variant is a variant with the structural stability which is increased under certain physical or chemical conditions, or physiological activity which is increased.

Nucleic acids including nucleotide sequences encoding the Oct4, Sox2, Klf4, and Glis1 proteins are nucleic acids including nucleotide sequences encoding wild type Oct4, Sox2, Klf4, and Glis1 proteins or Oct4, Sox2, Klf4, and Glis1 proteins in the form of the variant as described above, may be modified by substitution, deletion, and insertion of one or more bases, or a combination thereof, and may be naturally isolated or prepared using a chemical synthesis method.

The nucleic acid having nucleotide sequences encoding Oct4, Sox2, Klf4, and Glis1 proteins may be a single chain or a double chain, and may be a DNA molecule (genome, cDNA) or an RNA molecule. In specific exemplary embodiments of the present invention, synthetic messenger RNA (mRNA) was used as the nucleic acid encoding the Oct4, Sox2, Klf4, and Glis1 proteins, and the synthetic messenger RNA may be prepared using a synthetic mRNA expression vector into which DNA expressing Oct4, Sox2, Klf4, and Glis1 is introduced.

The present invention provides a method for direct reprogramming of urine cells into neural stem cells, the method, comprising; introducing Oct4, Sox2, Klf4, and Glis1 proteins or nucleic acids encoding the proteins into urine cells.

More specifically, the method may comprise:
(a) isolating urine cells from urine and culturing the urine cells;
(b) introducing the composition of claim 1 or 3 into the cultured urine cells;
(c) inducing direct reprogramming into neural stem cells by culturing urine cells into which the composition has been introduced in a neural stem cell-inducing medium; and
(d) selecting a neural stem cell line having characteristics similar to neural stem cell from the cells in which direct reprogramming has been induced by the neural stem cell-inducing medium.

In step (a), urine cells may be cultured in a medium containing fetal bovine serum (FBS), a basic fibroblast growth factor (bFGF), and an epithelial growth factor (EGF).

As used herein, the term "culture medium" refers to a medium capable of supporting the growth and survival of cells in vitro, and include all the typical media used in the art suitable for the induction and culture of urine cells and reprogrammed neural stem cells. According to the type of cell, culture medium and culture condition may be selected. The culture medium used for the culture is preferably a cell culture minimum medium (CCMM), and generally includes a carbon source, a nitrogen source, and a trace element component. Examples of such a cell culture minimum medium include a Dulbecco's Modified Eagle's Medium (DMEM), a Minimal Essential Medium (MEM), a Basal Medium Eagle (BME), RPMI1640, F-10, F-12, an α Minimal Essential Medium (αMEM), a Glasgow's Minimal Essential Medium (GMEM), Iscove's Modified Dulbecco's Medium (IMEM), and the like, but are not limited thereto. Further, the culture medium may include an antibiotic such as penicillin, streptomycin, or gentamicin.

In a specific example of the present invention, the culture medium may be obtained by culturing the cells isolated from urine in a basal medium containing FBS, bFGF, and EGF, and specifically, the culture medium may be obtained by adding bFGF and EGF to high glucose DMEM and renal epithelial cell growth medium (REGM) media including FBS and culturing the cells isolated from urine in the culture media. More specifically in the present invention, the high glucose DMEM and REGM media may additionally include L-glutamine and penicillin-streptomycin.

In step (b), as the method of introducing a reprogramming factor into urine cells, a method of providing a nucleic acid or protein into cells typically used in the art may be used without limitation, and preferably, it is possible to use a method of administering a reprogramming factor into a culture solution of differentiated cells or a method of directly injecting a reprogramming factor into differentiated cells, and the reprogramming factor used in this case may be used in the form of a virus obtained from packaging cells transfected with a viral vector into which the gene of the corresponding factor has been inserted, messenger RNA produced by in vitro transcription, a protein produced in various cell lines, or the like. In specific exemplary embodiments of the present invention, in the introduction of the reprogramming factor into urine cells, messenger RNA produced by transcription of the DNA encoding Oct4, Sox2, Klf4, and Glis1 was used.

As a method of directly injecting the synthetic messenger RNA into differentiated cells, any method known in the art may be selected and used, and a method may be appropriately selected and applied from methods using microinjection, electroporation, particle bombardment, direct muscle injection, an insulator, and a transposon. Specifically, in exemplary embodiments of the present invention, the messenger RNA of the reprogramming factor was introduced into urine cells using electroporation.

In step (c), a medium (a neural stem cell-inducing medium) that induces urine cells, into which nucleic acids encoding Oct4, Sox2, Klf4, and Glis1 proteins have been introduced, into neural stem cells may be a medium obtained by mixing a DME/MF12 medium and a neurobasal medium at a volume ratio of 1:1, and adding 1×N2, 1×B27, human LIF, a TGF-beta inhibitor, and a GSK3-beta inhibitor to the medium mixture. More specifically, the medium may further include one or more of a Shh agonist, an adenylyl cyclase activator, a histone deacetylase inhibitor, and ascorbic acid 2-phosphate. In the specific exemplary embodiments of the present invention, it was confirmed that the neural stem cell conversion rate was the best in a medium supplemented with all of the Shh agonist, the adenylyl cyclase activator, the histone deacetylase inhibitor, and ascorbic acid 2-phosphate.

In addition, when urine cells are cultured in the medium under low oxygen ($O_2$ hypoxia) conditions, induction efficiency may be increased.

The selection of neural stem cells induced in step (d) is for collecting the neural stem cell colonies produced after step (c) is performed, and the selected neural stem cells may be cultured in the neural stem cell medium. The neural stem cell medium may be a medium obtained by adding 1×N2, 1×B27, human LIF, a TGF-beta inhibitor and a GSK3-beta inhibitor to a medium in which a DMEM/F12 medium and a neurobasal medium are mixed at a volume ratio of 1:1. Furthermore, the induced neural stem cells may be subcultured using a 0.5 mM EDTA solution or an Accutase solution.

Further, the present invention provides a pharmaceutical composition for the prevention or treatment of neurological damage diseases comprising the neural stem cells induced by the method as an active ingredient.

Further, the present invention provides a method for the prevention or treatment of neurological damage diseases comprising administering the directly reprogrammed neural stem cells prepared by the method as an active ingredient.

Neural stem cells are multi-potent cells that can differentiate into nerve cells (neurons), astrocytes, oligodendrocytes, GABAergic nerve cells, dopaminergic nerve cells, or the like, and can repair or restore damaged or lost nerve cells, so that it is possible to treat diseases caused by the damage or disappearance of nerve cells without limitation.

Specifically, the disease caused by the damage to nerve cells may be selected from the group consisting of Parkinson's disease, Alzheimer's disease, Pick's disease, Huntington's disease, amyotrophic lateral sclerosis, an ischemic brain disease (stroke), a demyelinating disease, multiple sclerosis, epilepsy, a degenerative neurological disease, and spinal cord injury.

Advantageous Effects

The present invention is a technique which utilizes human urine-derived cells as a cell source to maximize the convenience of securing the cell source, and enhances clinical feasibility by a non-integrative direct reprogramming method using synthetic mRNA.

DESCRIPTION OF DRAWINGS

FIG. 6 illustrates the results of confirming whether induced neural stem cells have the ability to differentiate through immunostaining of Ki67.

FIG. 7 illustrates the results of confirming whether induced neural stem cells express neural stem cell marker genes such as SOX1, SOX2, PLZF, and PAX6 compared to neural stem cells derived from H9 embryonic stem cells through quantitative analysis of mRNA by qRT-PCR.

FIG. 11 illustrates the results of confirming whether synthetic mRNA introduced into neural stem cells remains in a host and whether the synthetic mRNA is integrated into a host genome, through RT-PCR and genomic DNA PCR analysis of a VEE gene.

FIG. 12 illustrates the results of confirming whether induced neural stem cells are derived from human urine cells through STR analysis.

FIG. 15 illustrates the results of confirming through immunostaining that induced neural stem cells can differentiate into GABA nerve cells, motor nerve cells, and dopamine nerve cells.

FIG. 16 illustrates the results of confirming the expression of S100beta and GFAP, which are markers for verifying the ability of induced neural stem cells to differentiate into astrocytes, which are glial cells, by an immuno-screening method.

FIG. 17 illustrates the results of confirming the expression of PDGFR, OLIG2, and O4, which are markers for verifying the ability of induced neural stem cells to differentiate into oligodendrocytes, which are glial cells, by an immuno-screening method.

FIG. 18 illustrates the results of confirming the relative mRNA expression levels of OCT4, REX4, and NANOG by date in the process of inducing from urine cells to neural stem cells.

FIG. 19 illustrates the results of confirming whether the marker genes of H9 embryonic stem cells and induced neural stem cells at the pluripotent stage are expressed.

FIG. 20 illustrates the results of comparing the conversion rate when urine-derived cells are induced into neural stem cells under low oxygen conditions (5% hypoxia) using a basic condition (21% $O_2$) as a control.

FIG. 21 illustrates the results of confirming that the induction efficiency of neural stem cells is increased when one or more of a Shh agonist, an adenylyl cyclase activator, a histone deacetylase inhibitor, and ascorbic acid 2-phosphate are further included in a medium obtained by mixing a DMEMF12 medium and a neurobasal medium at a volume ratio of 1:1, and adding 1×N2, 1×B27, human LIF, a TGF-beta inhibitor, and a GSK3-beta inhibitor to the medium mixture. It was confirmed that the neural stem cell conversion rate was the best in a medium supplemented with all of the Shh agonist, the adenylyl cyclase activator, the histone deacetylase inhibitor, and ascorbic acid 2-phosphate.

MODES OF THE INVENTION

Hereinafter, the present invention will be described in more detail with reference to Examples. However, the following Examples are provided only to more easily understand the present invention, and the present invention is not limited to the following Examples.

Example 1: Isolation of Urine Cells from Urine

Based on a technique developed by Sutherland and Bain in the United Kingdom in 1972, the specifics are as follows. First, the urine donated by a donor was centrifuged at 1000 g for 10 minutes. After the supernatant was removed, the pellet remaining in the lower layer was diluted with 20 ml of a PBS solution containing 1% Penicillin/Streptomycin/Amphotericin B antibiotics. The diluted PBS+pellet solution was then centrifuged at 1000 g for 10 minutes. After the supernatant was removed again, the pellet remaining in the lower layer was diluted with 1 ml of a basal medium (a medium including 1% Penicillin/Streptomycin Amphotericin B antibiotics, 1% L-glutamine, and 10% FBS based on DMEMF12) and seeded onto a 12-well cell culture dish coated with gelatin. Then, after cells were cultured by adding 1 ml of the basal medium for 3 days, the cells were cultured by changing the medium to a growth medium (a medium including 1% Penicillin/Streptomycin antibiotics, 1% L-glutamine, 5% FBS, 10 ng/ml bFGF, and 10 g/ml EGF based on a medium obtained by mixing DMEM and REGM at 1:1).

Figure 1:
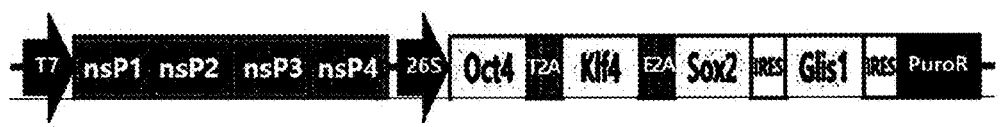
FIG. 1 is a schematic view of a T7-VEE-OKS-iG vector for preparing synthetic mRNAs of OCT4, KLF4, SOX2, and GLIS1 genes.

Example 2: Introduction of Reprogramming Factor into Urine Cells Using Electoporation A method of introducing synthetic mRNA into urine-derived cells cultured in Example 1 by electroporation is specifically as follows. Synthetic mRNA is synthesized through a typical in vitro transcription kit (RiboMAX® Large Scale RNA Production Systems, Promega), and DNA, which becomes a backbone of mRNA to be synthesized, is T7-VEE-OKS-iG (Steven Dowdy, Addgene), which includes genes of OCT4, KLF4, SOX2, and GLIS1 (FIG. 1). As the sequences of the OCT4, KLF4, SOX2, and GLIS1 genes, those disclosed in Nature. 2011 Jun. 8; 474(7350): 225-9. were used, and for the corresponding gene sequence and mRNA application method, Cell Stem Cell. 2013 Aug. 1; 13 (2): 246-54 and U.S. Pat. No. 9,862,930 B2 were referenced.

The synthesized mRNA was introduced by treating $1\times10^6$ urine-derived cells pretreated with 0.2 ug/ml of B18R protein with 0.5 µg of the synthesized mRNA 3 times by electroporation at 1600 V and 10 ms for 1 hour. The introduced urine-derived cells were cultured in a growth medium including 0.2 ug/ml of B18R protein for 2 days.

Figure 2:
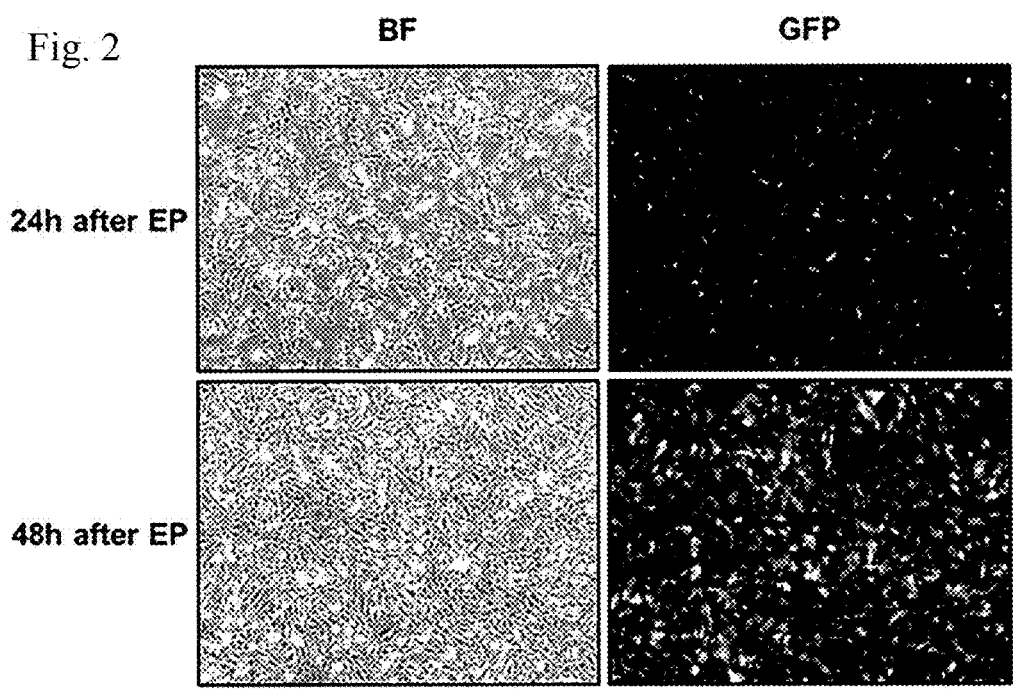
FIG. 2 illustrates the results confirming whether synthetic mRNAs of OCT4, KLF4, SOX2, and GLIS1 genes to which GFP (fluorescent gene) is bound are introduced into urine cells through FACS analysis.
Figure 2:
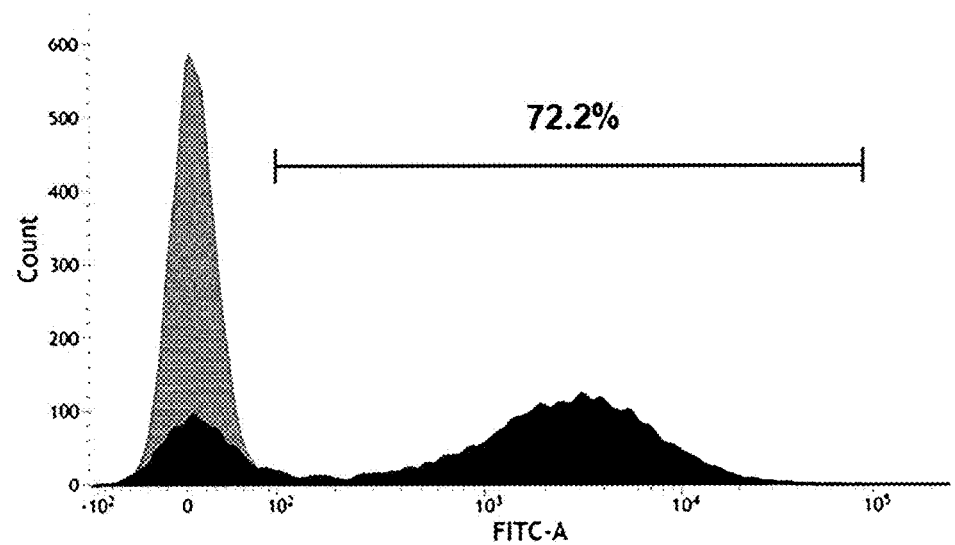

The present inventors verified the efficiency of human urine-derived cells expressing a GPF fluorescence protein through FACS analysis by simultaneously introducing the synthetic mRNA including the GFP fluorescence protein in order to visualize, determine, and verify the efficiency of introduction through electroporation. By confirming through the verification that the human urine-derived cell introduction efficiency of synthetic mRNA by electroporation reached 72.2% around 48 hours after treatment, it was determined that it was sufficient to perform a neural stem cell induction experiment which is the next step (FIG. 2).

Example 3: Induction of Reprogrammed Neural Stem Cells Derived from Urine

Figure 3:
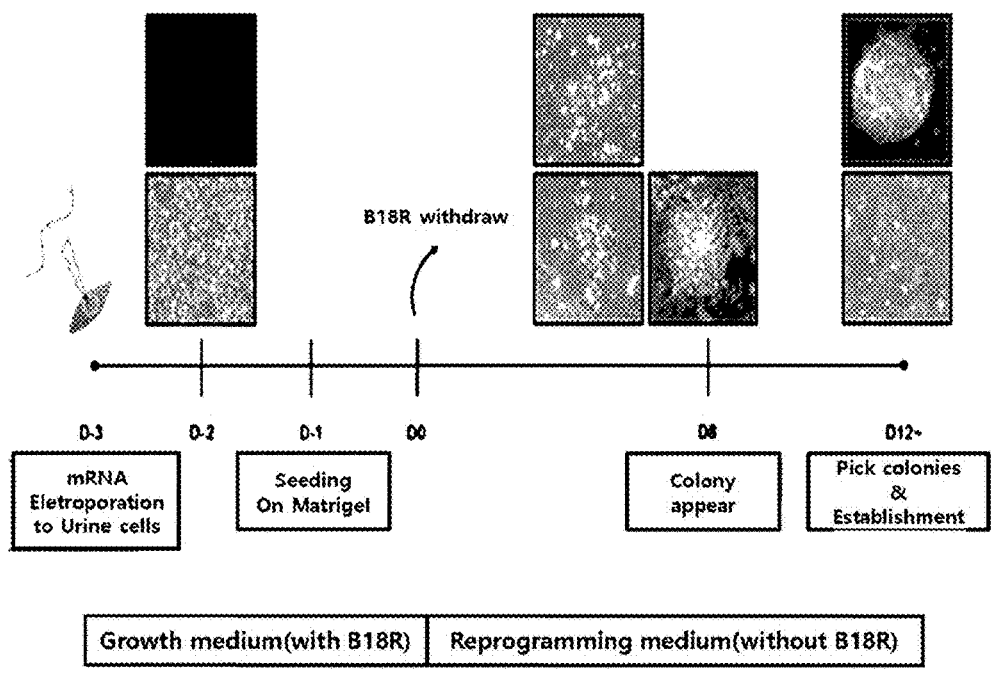
FIG. 3 illustrates the entire process of obtaining a colony of neural stem cells derived from urine cells using a direct reprogramming technique.

After mRNA-introduced urine-derived cells were seeded in a cell culture dish coated with Matrigel™, the cells were cultured in a neural stem cell-inducing medium supplemented with 0.5 uM purmorphamine (Shh agonist), 10 uM forskolin (adenylyl cyclase activator), 100 uM sodium butyrate (histone deacetylase inhibitor), and 64 ug/ml ascorbic acid 2-phosphate based on a neural stem cell-inducing medium (a medium obtained by mixing a DMEM/F12 medium and a neurobasal (Gibco) medium at 1:1 and adding 1×N2 (Gibco), 1×B27 (Gibco), 10 ng/ml human LIF, 2 uM SB431542 (TGF-beta inhibitor), and 3 uM CHIR99021 (GSK3-beta inhibitor) to the medium mixture) for 7 to 10 days. The development of neural stem cell colonies could be confirmed when the induction was completed (FIG. 3).

Further, effects on the induction efficiency of neural stem cells were confirmed when one or more of a Shh agonist, an adenylyl cyclase activator, a histone deacetylase inhibitor, and ascorbic acid 2-phosphate were further included in a medium further supplemented with 1×N2, 1×B27, human LIF, a TGF-beta inhibitor and a GSK3-beta inhibitor. It was confirmed that the neural stem cell conversion rate was the best in a medium supplemented with all of the Shh agonist, the adenylyl cyclase activator, the histone deacetylase inhibitor, and ascorbic acid 2-phosphate (FIG. 21).

The induced neural stem cell colonies were collected, and cultured by placing the neural stem cell medium in a cell culture dish coated with Matrigel. The induced neural stem cells could then be subcultured using a 0.5 mM EDTA solution or an Accutase solution, and then experiments of verifying the various properties of the induced neural stem cells in the following examples were conducted.

Figure 4:
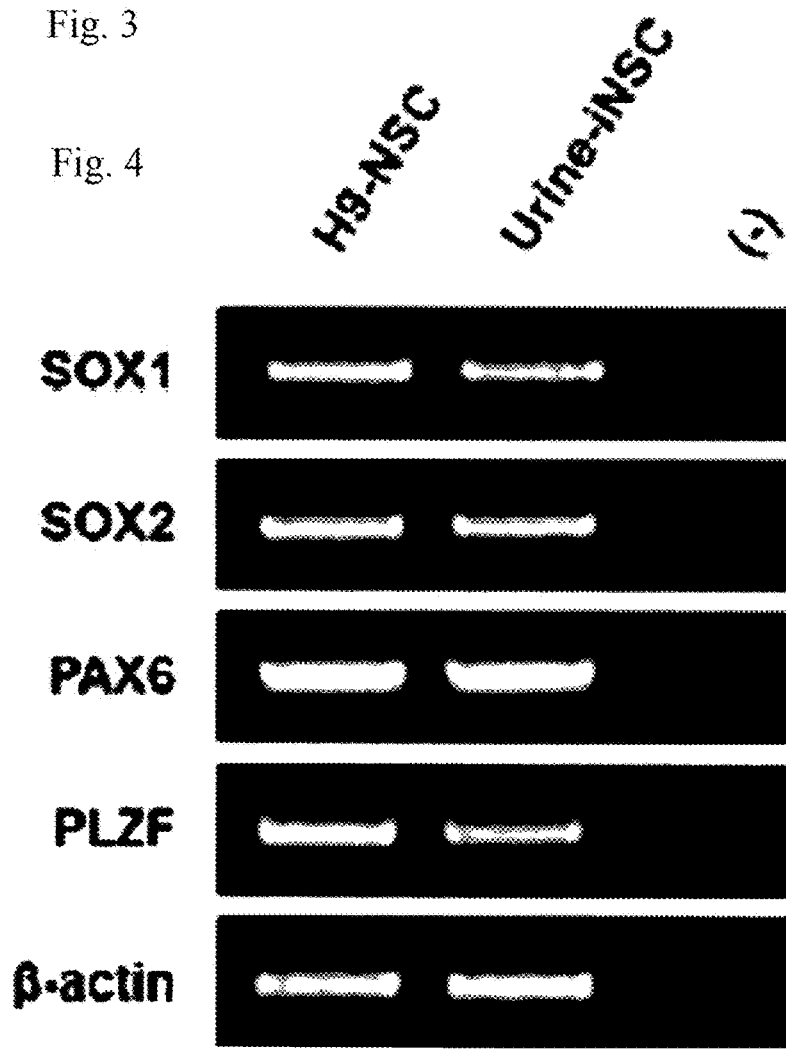
FIG. 4 illustrates the results of confirming whether induced neural stem cells express neural stem cell marker genes such as SOX1, SOX2, PAX6, and PLZF through mRNA level analysis by RT-PCR using neural stem cells derived from H9 embryonic stem cells as a positive control.

Example 4: Analysis of Molecular Biological Properties of Induced Neural Stem Cells Experiments were conducted to verify the molecular biological properties of neural stem cells derived from the present invention.
<4-1>
It was confirmed that neural stem cells induced through mRNA level analysis by RT-PCR using neural stem cells derived from H9 embryonic stem cells as a positive control expressed neural stem cell marker genes such as SOX1, SOX2, PAX6, and PLZF (FIG. 4). The sequences of primers used in the present experiment are as follows:

SOX1 (forward-ACACTTGAAGCCCAGATGG; SEQ ID NO: 1, reverse-ATAGGCTCACTTTTGGACGG; SEQ ID NO: 2), SOX2 (forward-TCAGGAGTTGTCAAGGCAGAGA; SEQ ID NO: 3, reverse-CCGCCGCCGATGATTGTTATTA; SEQ ID NO: 4), PAX6 (forward-GGCTCAAATGCGACTTCAG; SEQ ID NO: 5, reverse-CCCTTCGATTAGAAAACCATACC; SEQ ID NO: 6), PLZF (forward-TATACAGCCACGCTGCAAGCCA; SEQ ID NO: 7, reverse-TGGTCTCCAGCATCTTCAGGCA; SEQ ID NO: 8).

Figure 5:
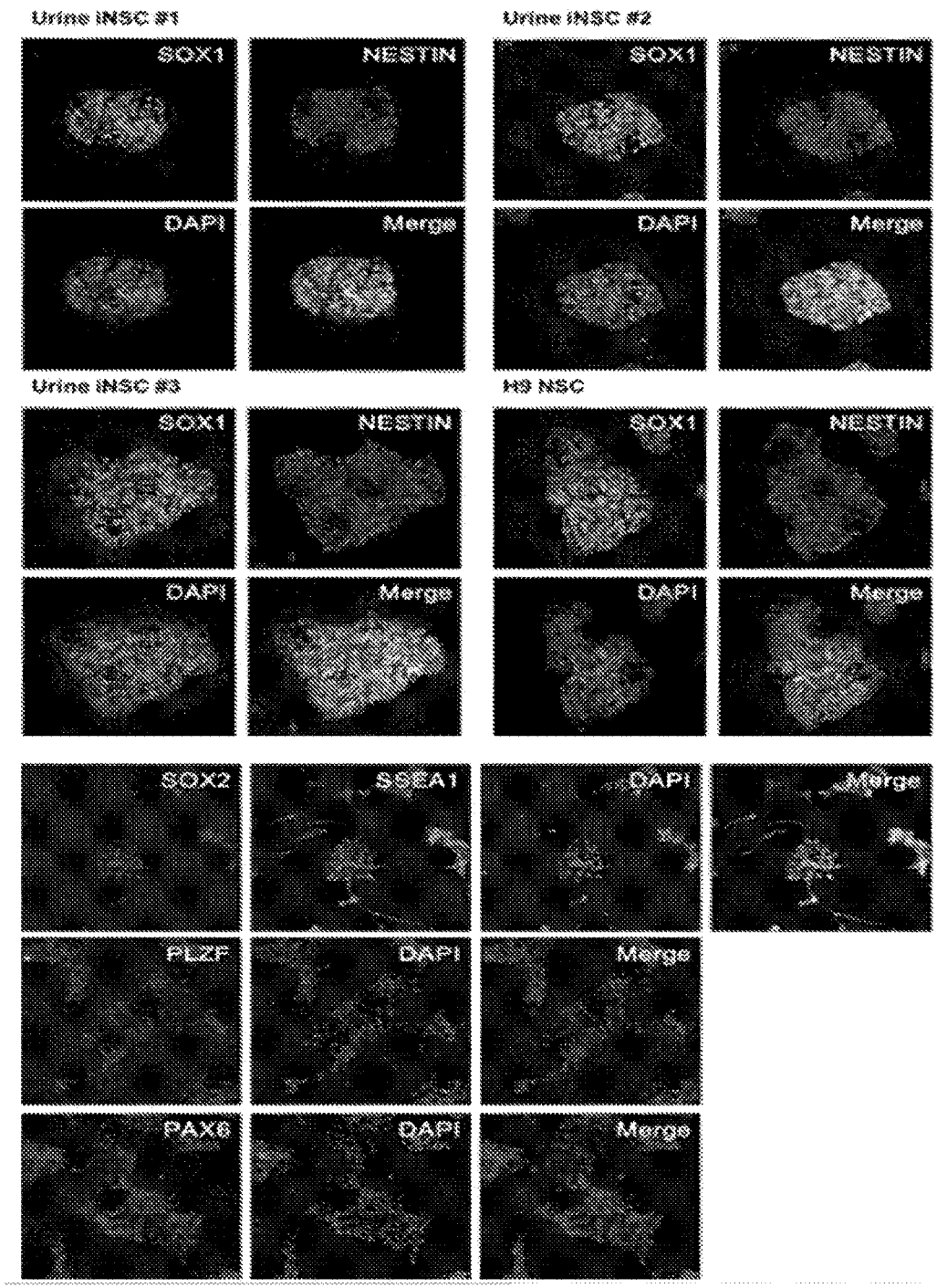
FIG. 5 illustrates the results of confirming whether induced neural stem cells express neural stem cell marker genes such as SOX1, NESTIN, SSEA1, SOX2, PAX6, and PLZF at the protein level through immunoassay.
Figure 8:
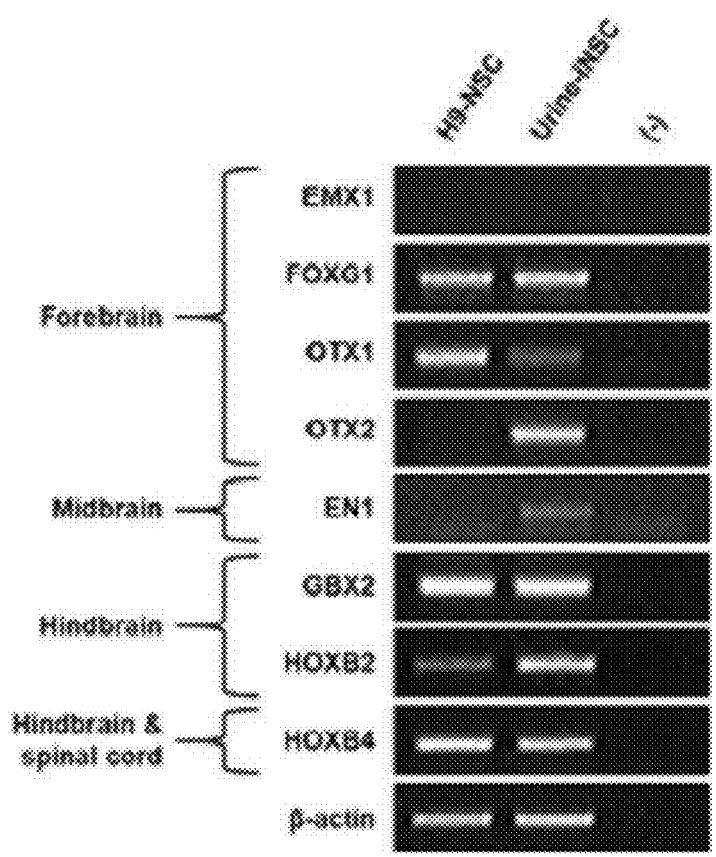
FIG. 8 illustrates the results of confirming whether induced neural stem cells express developmental forebrain, midbrain, hindbrain, and spinal cord-specific marker genes through mRNA level analysis by RT-PCR.
Figure 9A:
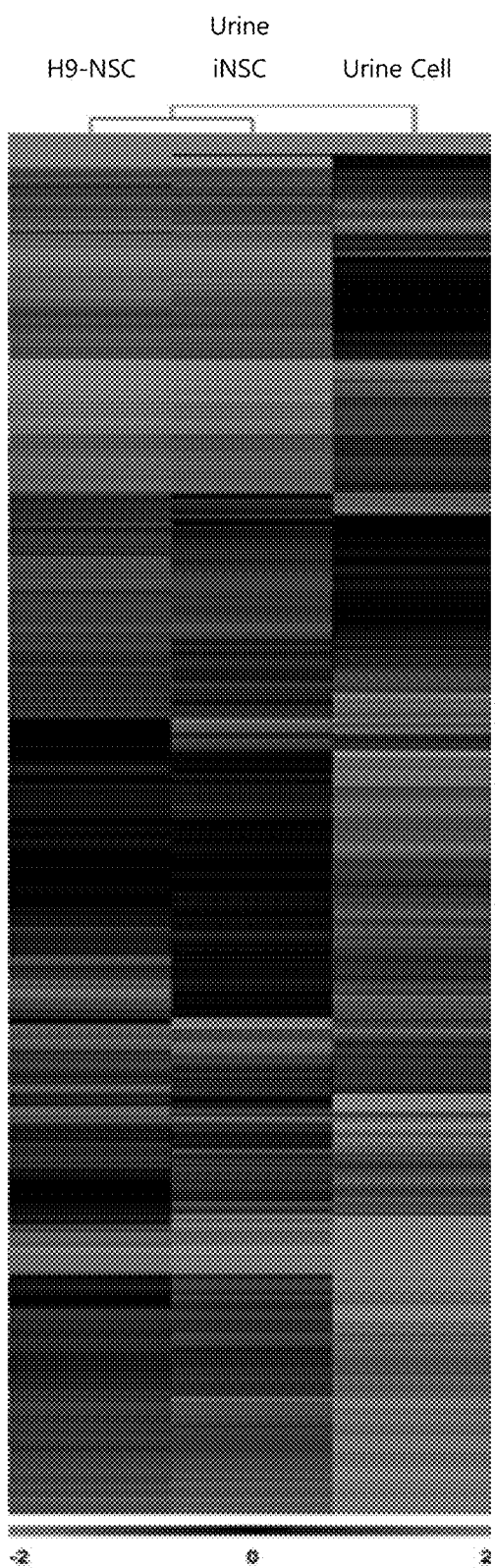
FIGS. 9 and 10 illustrate the results of confirming whether the induced neural stem cells exhibit mRNA and long non-coding-RNA (lnc-RNA) expression patterns more similar to those of neural stem cells derived from H9 embryonic stem cells than original urine-derived cells through total RNA sequencing at the global gene expression level.
Figure 9B:
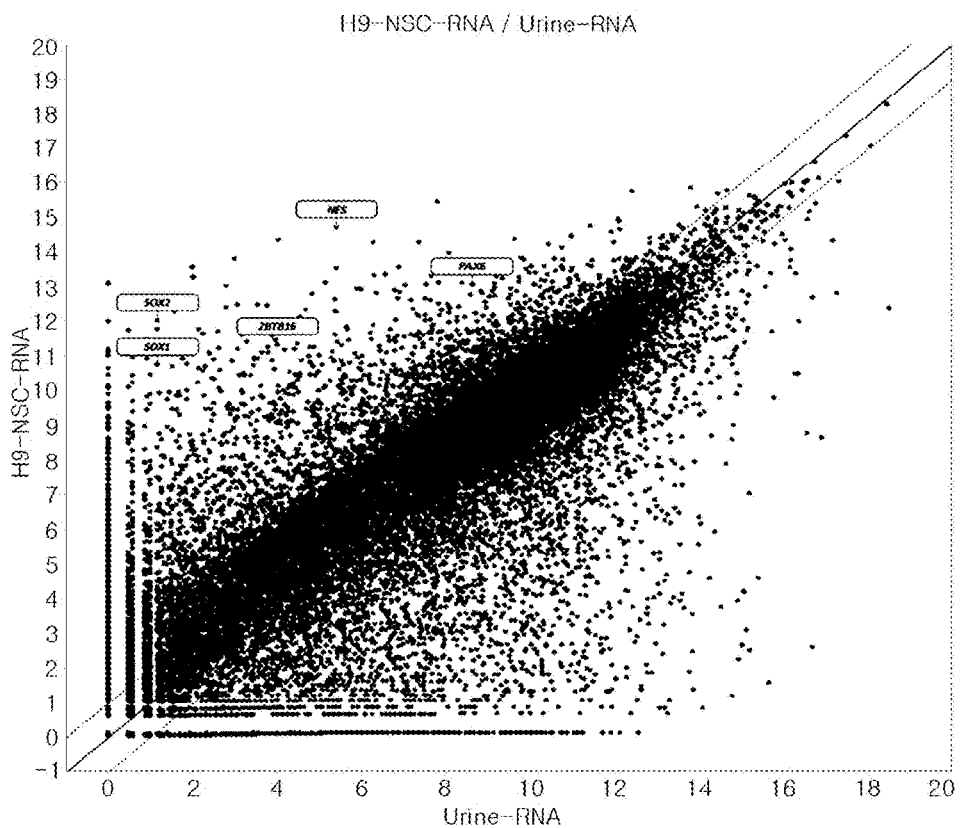
Figure 9C:
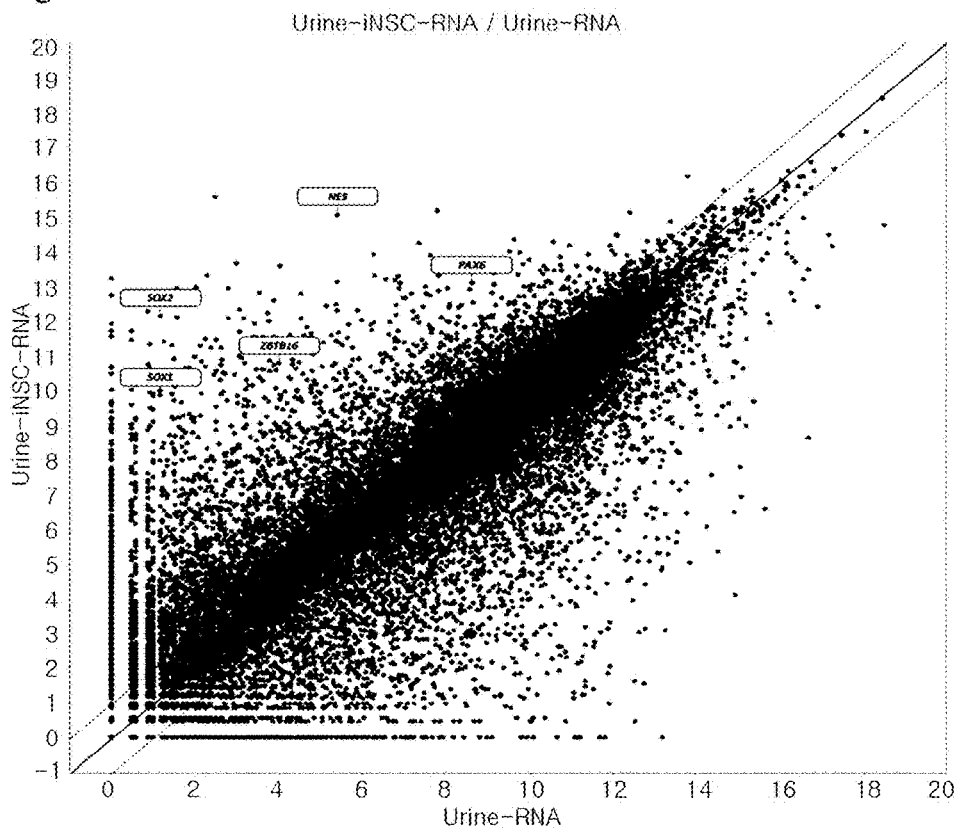
Figure 9D:
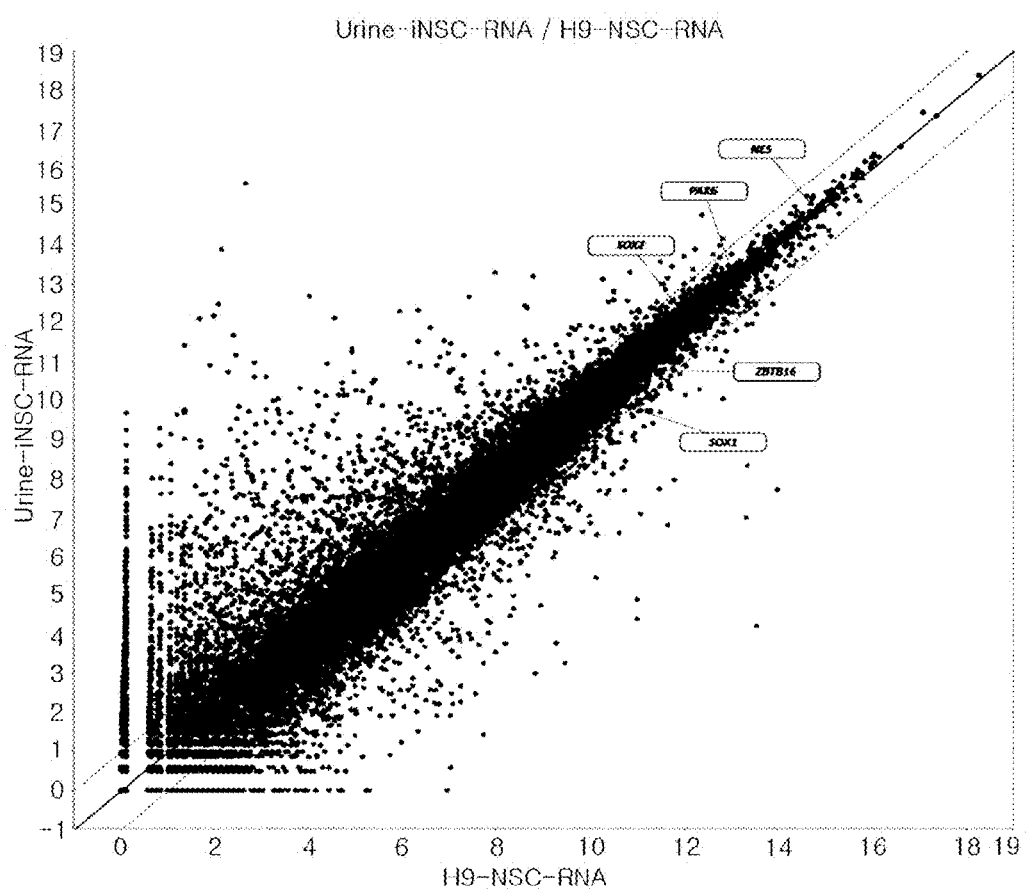

<4-2>
It was also confirmed through a protein level analysis using immunostaining that induced neural stem cells expressed neural stem cell marker genes such as SOX1, NESTIN, SSEA1, SOX2, PAX6, and PLZF (FIG. 5). The antibodies used in the present experiment are as follows: SOX1 (AF3369, R&D Systems), NESTIN (MAB5326, Millipore), SSEA1 (MAB4301, Millipore), SOX2 (SC-20088, Santacruz), PAX6 (PAX6, DSHB), PLZF (AF2944, R&D Systems).
<4-3>
It was confirmed through immunostaining of Ki67 that neural stem cells induced have a cell division ability (FIG. 6). The antibodies used in the present experiment are as follows: Ki67 (Ab9260, Millipore).
<4-4>
It was also confirmed through quantitative analysis of mRNA by qRT-PCR that induced neural stem cells expressed neural stem cell marker genes such as SOX1, SOX2, PLZF, and PAX6, compared to neural stem cells derived from H9 embryonic stem cells (FIG. 7).
<4-5>
It was also confirmed through mRNA level analysis by RT-PCR that induced neural stem cells expressed developmental forebrain, midbrain, hindbrain, and spinal cord-specific marker genes (FIG. 8). The sequences of primers used in the present experiment are as follows:

EMX1 (forward-CAGGCCCAGGTAGTTCAATGGG; SEQ ID NO 9, reverse-GCTCAGCCTTAAGCCCTGTCTC; SEQ ID NO: 10), FOXG1 (forward-ACCCGTCAATGACTTCGCAGAG; SEQ ID NO: 11, reverse- AGGGTTGGAAGAAGACCCCTGA; SEQ ID NO: 12), OTX1

(forward-CTCAAACAACCCCCATACGGCA; SEQ ID NO: 13, reverse-GGTAGCGAGTCTTGGCGAAGAG; SEQ ID NO: 14), OTX2 (forward-TTCAGGGCTGTGTGAATTGTGTGA; SEQ ID NO: 15, reverse-CAGAGGTGGAGTTCAAGGTTGCAT; SEQ ID NO: 16), EN1 (forward-GAGTTCCAGGCAAACCGCTACA; SEQ ID NO: 17, reverse-GTTGTACAGTCCCTGGGCCATG; SEQ ID NO: 18), GBX2 (forward-CGGTTAGCAGCCACCTTTCCAT; SEQ ID NO: 19, reverse-GACGTGCTTCACATGGCTCAGA; SEQ ID NO: 20), HOXB2 (forward-GAGACCCAGGAGCCAAAAGC; SEQ ID NO: 21, reverse-GAAGGAGACGTGGCGGATTG; SEQ ID NO: 22), HOXB4 (forward-CTGAGGGCCAGAATGACTGCTC; SEQ ID NO: 23, reverse-CAGAACTCAACTGGCCCCTCAC; SEQ ID NO: 24).

Figure 10A:
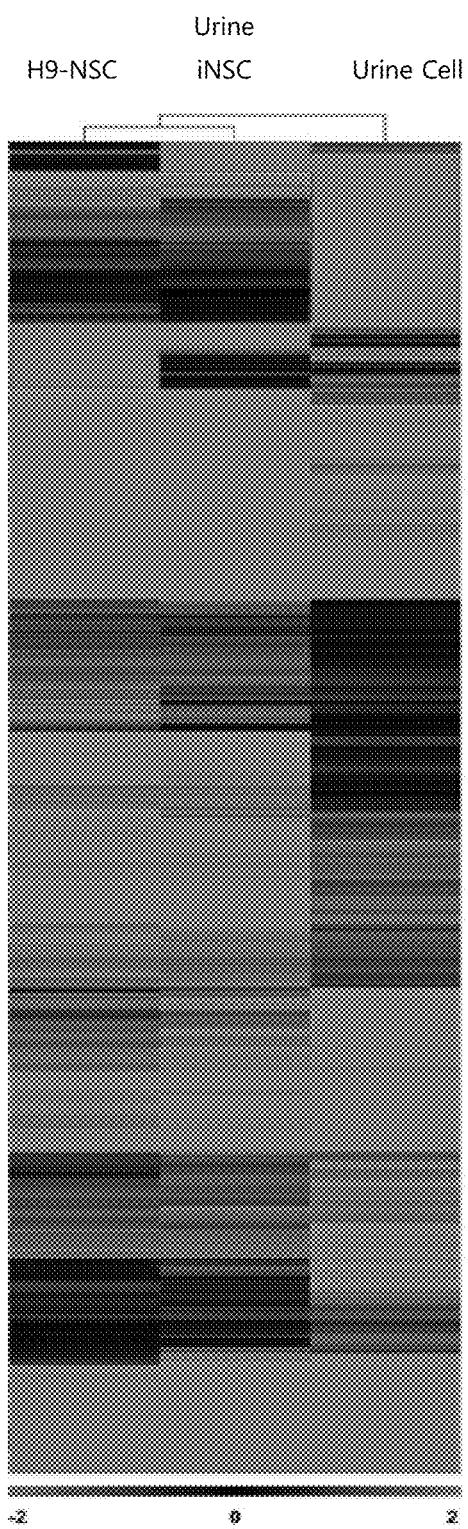
Figure 10B:
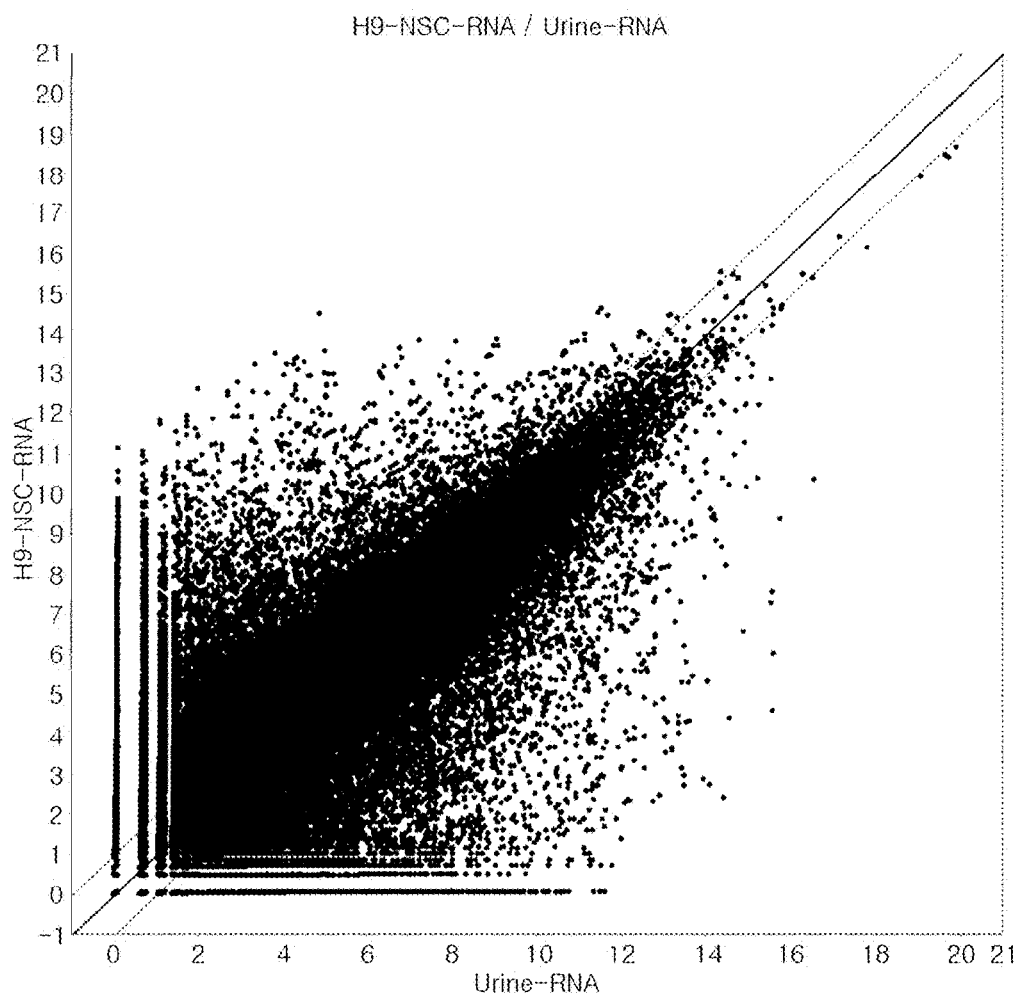
Figure 10C:
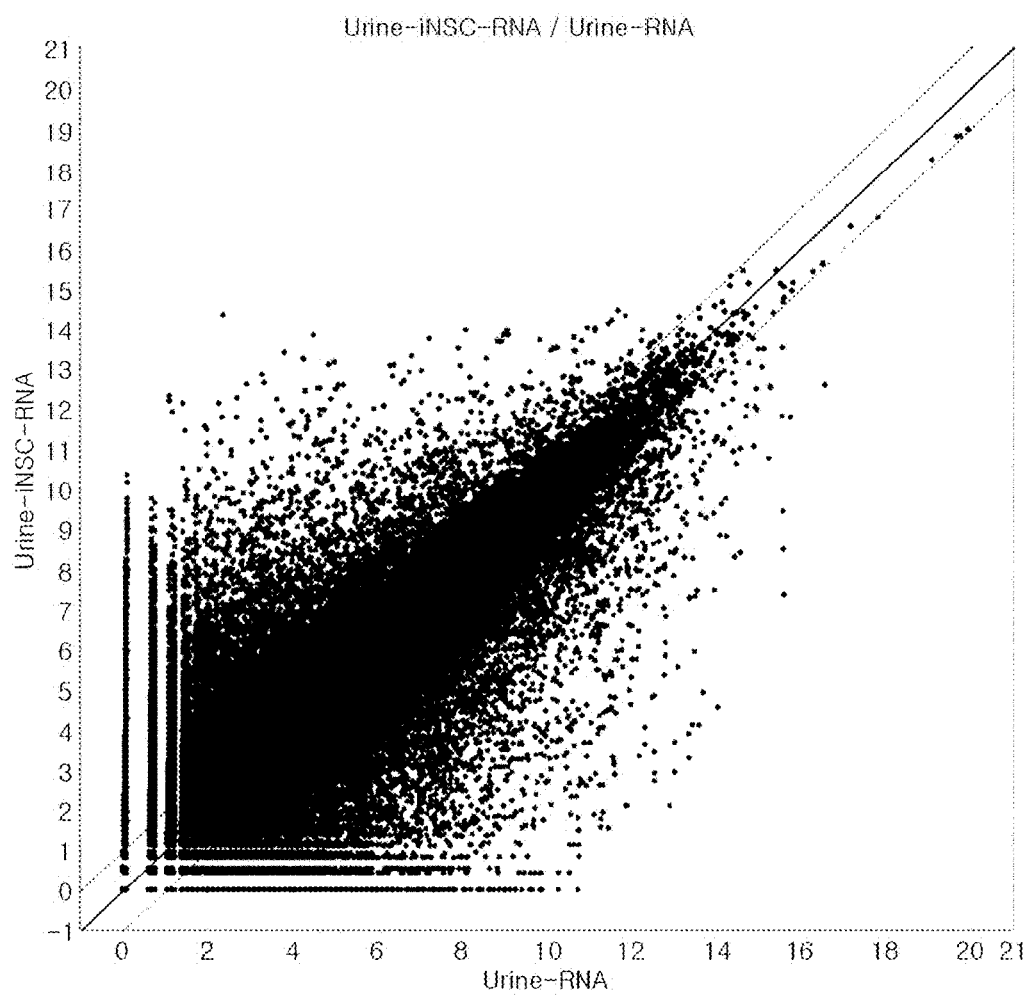

<4-6>
It was confirmed through total RNA sequencing at the global gene expression level that the induced neural stem cells exhibited mRNA and lnc-RNA expression patterns more similar to those of neural stem cells derived from H9 embryonic stem cells than original urine-derived cells (FIGS. 9 and 10).
<4-7>
It was confirmed through RT-PCR and genomic DNA PCR analysis of a VEE gene that synthetic mRNA introduced into neural stem cells no longer remained in a host, and was not integrated into a host genome (FIG. 11). The sequences of primers used in the present experiment are as follows:

VEE (forward-ACGAAGGGCAAGTCGCTGTT; SEQ ID NO: 25, reverse-TTTCGTCGGCCCAGTTGGTA; SEQ ID NO: 26).

Figure 13:
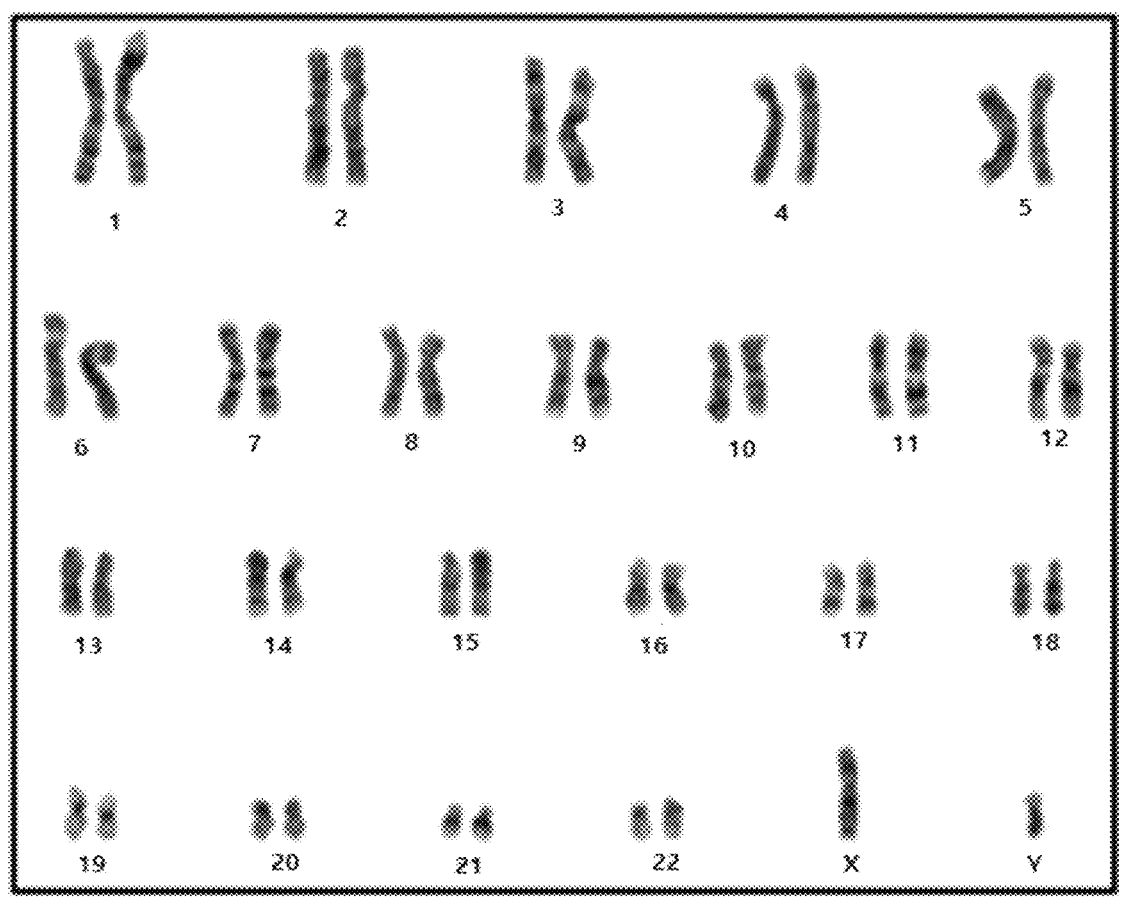
FIG. 13 illustrates the results of confirming whether induced neural stem cells preserve normal chromosomes through karyotype analysis.

<4-8>
It was confirmed through STR analysis that human urine cells and induced neural stem cells were derived from the same individual (FIG. 12).
<4-9>
It was confirmed through karyotype analysis that induced neural stem cells preserved normal chromosomes (FIG. 13).

Example 5: Analysis of Ability of Induced Neural Stem Cells to Differentiate

Figure 14:
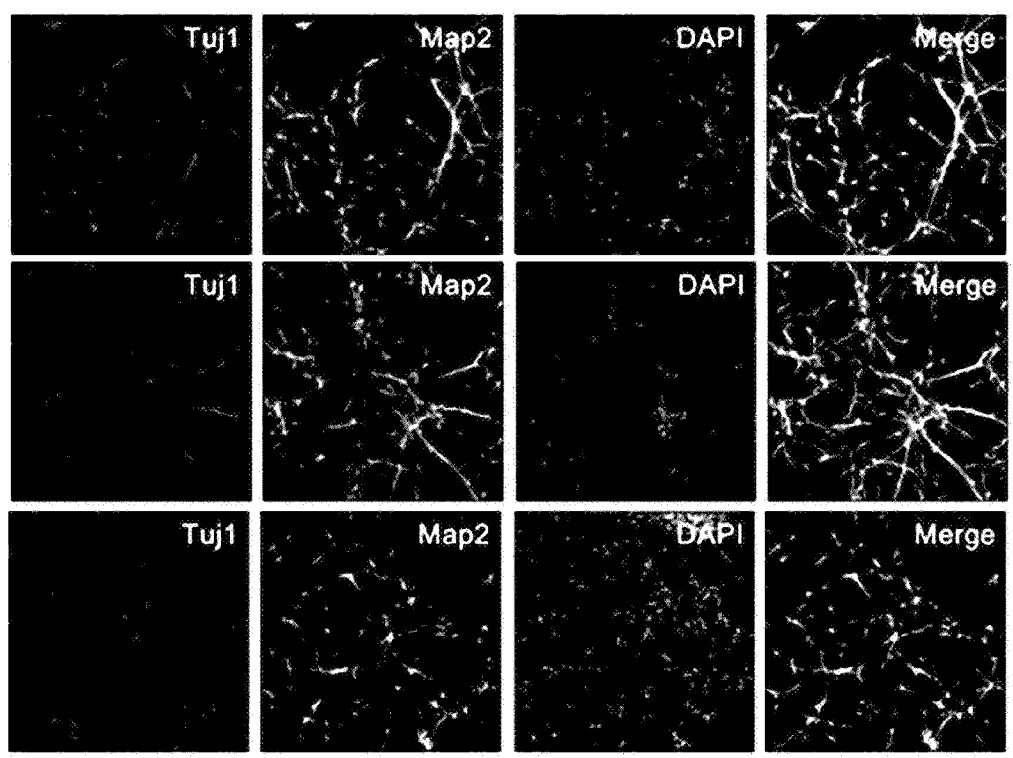
FIG. 14 illustrates the results of confirming the expression of the nerve cell gene markers TUJ1 and MAP2 by an immuno-screening method in order to verify the ability of the induced neural stem cells to differentiate into nerve cells.

<5-1> Analysis of Ability to Differentiate into Nerve Cells
It was confirmed through immunostaining that neural cell marker genes TUJ1 and MAP2 were expressed when the induced neural stem cells were differentiated into nerve cells (FIG. 14). The nerve cell differentiation method is as follows. Neural stem cells are analyzed after being cultured in a nerve cell differentiation medium obtained by adding 1×N2, 1×B27, 300 ng/ml cAMP, 0.2 mM vitamin C, 10 ng/ml BDNF, and 10 ng/ml GDNF to a DMEM/F12 medium for 14 days. The antibodies used in the present experiment are as follows. Tuj1 (801202, BioLegend), MAP2 (AB5622, Millipore)

Further, it could be confirmed that the induced neural stem cells could differentiate into GABA nerve cells, motor nerve cells, and dopamine nerve cells by staining GABA, HB8, and TH, respectively through immunostaining (FIG. 15).

The antibodies used in the present experiment are as follows: GABA (A2052, Sigma), HB9 (81.5C10, DSHB), TH (AB152, Millipore).

<5-2> Analysis of Ability to Differentiate into Glial Cells

It was confirmed that the induced neural stem cells could differentiate into astrocytes, which are one of the glial cells, through S100beta and GFAP staining through immunostaining (FIG. 16). The astrocyte differentiation method is as follows. Induced neural stem cells are cultured in an astrocyte differentiation medium supplemented with 2.5% FBS or 20 ng/ml CNTF, and 10 ng/ml BMP4 in a medium containing 1×N2 and 1×B27 in a DMEM/F12 medium for 14 days or more, and then analyzed. The antibodies used in the present experiment are as follows: S100beta (S2535, Sigma), GFAP (SAB4501162, Sigma).

It was confirmed that the induced neural stem cells could differentiate into oligodendrocytes, which are one of the glial cells, through PDGFR, OLIG2, and O4 staining through immunostaining (FIG. 17). The oligodendrocyte differentiation method is as follows. After induced neural stem cells are cultured in a medium obtained by adding 1×N2, 1×B27, 25 ug/ml insulin, 1 uM Shh agonist, and 100 nM retinoic acid to a DMEM/F12 medium for 5 days or more, the cells are cultured in a medium obtained by adding 1×N2, 1×B27, 25 ug/ml insulin, 100 ng/ml biotin, 60 ng/ml T3, 10 ng/ml PDGF-AA, 10 ng/ml IGF-1, 5 ng/ml HGF, 10 ng/ml NT-3, and 1 uM cAMP to a DMEM/F12 medium for 7 days or more, and then analyzed. The antibodies used in the present experiment are as follows: PDGFR (SC338, Santa Cruz), OLIG2 (AB9610, Millipore), O4 (MAB345, Millipore).

Example 6: Verification and Analysis of Neural Stem Cell Induction Method that does not go Through Pluripotent Stage It is known that the combination of the reprogramming factors OCT4, SOX2, KLF4, and GLIS1 genes used in the present invention can establish induced pluripotent stem cells under specific conditions (U.S. patent Ser. No. 09/862,930).

However, it was verified that the neural stem cells induced in the present invention do not go through the pluripotent stage for the following reasons.

First, a neural stem cell-inducing medium excluding bFGF, which is essential for establishing human-induced pluripotent stem cells, and a B18R protein, which is necessary for the expression of mRNA of an endogenous gene, was used, so that it is not possible to establish human-induced pluripotent stem cells according to the research results reported to date.

Second, the time when neural stem cells derived from the present invention are formed is around day 8 after the induction process according to the protocol (FIG. 3), and known human-induced pluripotent stem cells require a period of 3 weeks or more after the induction process to form, so that it is too short of a time to have gone through the pluripotent stage.

Third, when viewed by a date-based qRT-PCR analysis, the expression of the pluripotent stage marker genes OCT4, REX1 and NANOG maintained low expression from day 0 to day 12 (FIG. 18). The sequences of primers used in the present experiment are as follows.

```
GACAGGGGGAGGGGAGGAGCTAGG; SEQ ID NO: 27, reverse-
CTTCCCTCCAACCAGTTGCCCCAAAC; SEQ ID 28), REX1 (forward-CTGAAGAAACGGGCAAAGAC; SEQ ID NO:
29, reverse-GAACATTCAAGGGAGCTTGC; SEQ ID NO: 30), NANOG (forward-CAGCCCTGATTCTTCCACCAGTCCC; SEQ ID
NO: 31, reverse-GGAAGGTTCCCAGTCGGGTTCACC; SEQ ID
NO: 32).
```

Fourth, it was confirmed that when induced neural stem cells were verified through immunostaining, the expression of OCT4 and NANOG was not detected unlike the H9 embryonic stem cells (FIG. 19). The antibodies used in the present experiment are as follows: OCT4 (SC5279, Santa Cruz), NANOG (AF1997, R&D Systems).

Based on the points as described above, it could be confirmed that the method of the present invention could immediately induce urine cells into neural stem cells without going through the pluripotent stem cell stage.

Example 7: Experiment to Enhance Efficiency of Induction into Neural Stem Cells

Culture conditions capable of improving the efficiency of conversion to neural stem cells from urine cells, and the like were further confirmed.

Induction was performed by adjusting the oxygen concentration using general oxygen conditions (21% $O_2$) as a control. Specifically, after a neural stem cell induction method was performed on $1 \times 10^5$ urine-derived cells under basic conditions (21% $O_2$) and low oxygen conditions (5% hypoxia), respectively, it was confirmed by counting the number of colonies positive for neural stem cell marker genes SOX1 and PLZF using immunostaining that an approximate 2-fold increase in conversion efficiency was exhibited under low oxygen conditions (FIG. 20).

The invention claimed is:

1. A method for direct reprogramming of urine cells into neural stem cells, wherein direct reprogramming involves reprogramming of urine cells into neural stem cells without the intermediate generation of induced pluripotent stem cells (iPSCs), the method comprising:
   (a) isolating urine cells from urine and culturing the urine cells;
   (b) introducing into the cultured urine cells a composition comprising:
      (i) an Oct4 protein or a nucleic acid encoding the Oct4 protein;
      (ii) a Sox2 protein or a nucleic acid encoding the Sox2 protein;
      (iii) a Klf4 protein or a nucleic acid encoding the Klf4 protein; and
      (iv) a Glis1 protein or a nucleic acid encoding the Glis1 protein;
   (c) inducing direct reprogramming by culturing urine cells into which the composition has been introduced in a neural stem cell-inducing medium;
   (d) selecting a neural stem cell(s) expressing SOX1, SOX2, EN1 and PAX6 from the cultured urine cells in the neural stem cell-inducing medium, and
   wherein in step (c), the neural stem cell-inducing medium is obtained by mixing a DMEM/F12 medium and a neurobasal medium at a volume ratio of 1:1 and adding N2, B27, human LIF, a TGF-beta inhibitor, and a GSK3-beta inhibitor to the medium mixture.

2. The method of claim 1, wherein in step (b), the nucleic acid is a synthetic mRNA, and the introduction of the synthetic mRNA encoding the Oct4, Sox2, Klf4, and Glis1 proteins is by introducing the synthetic mRNA using electroporation.

3. The method of claim 1, wherein the neural stem cell-inducing medium further comprises one or more of a Shh agonist, an adenylyl cyclase activator, a histone deacetylase inhibitor, and ascorbic acid 2-phosphate.

4. The method of claim 3, wherein the culture in the neural stem cell-inducing medium is performed under $O_2$ hypoxia conditions.

* * * * *